US008931114B2

(12) United States Patent
Martin et al.

(10) Patent No.: US 8,931,114 B2
(45) Date of Patent: *Jan. 13, 2015

(54) ELASTOMERIC COMPOSITES WITH TETHER-CONTAINING, CONDUCTING POLYMERS FOR NANOSCALE DIFFUSION CONTROL

(75) Inventors: Brett D. Martin, Washington, DC (US); Martin H. Moore, Woodbridge, VA (US); Banahalli R. Ratna, Alexandria, VA (US); Gusphyl Justin, St. Louis, MO (US); Jawad Naciri, Herndon, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 644 days.

This patent is subject to a terminal disclaimer.

(21) Appl. No.: 13/296,920

(22) Filed: Nov. 15, 2011

(65) Prior Publication Data

US 2012/0073027 A1 Mar. 29, 2012

Related U.S. Application Data

(63) Continuation-in-part of application No. 12/564,270, filed on Sep. 22, 2009, now Pat. No. 8,120,893.

(60) Provisional application No. 61/098,905, filed on Sep. 22, 2008.

(51) Int. Cl.
*A41D 13/00* (2006.01)
*C07D 333/38* (2006.01)
*C08G 61/12* (2006.01)

(Continued)

(52) U.S. Cl.
CPC ............ *C07D 333/38* (2013.01); *C08G 61/126* (2013.01); *C08G 65/3324* (2013.01); *C08G 65/3344* (2013.01); *C08G 65/3346* (2013.01); *H01G 9/028* (2013.01); *C08G 65/3348* (2013.01); *C08G 2261/1424* (2013.01); *C08G 2261/1432* (2013.01); *C08G 2261/1452* (2013.01); *C08G 2261/44* (2013.01); *C08G 2650/50* (2013.01); *C08G 2261/135* (2013.01); *C08G 2261/1426* (2013.01); *C08G 2261/147* (2013.01); *C08G 2261/516* (2013.01)
USPC .................. 2/69; 252/500; 549/4; 549/72

(58) Field of Classification Search
CPC ............ A41D 13/00; C07F 5/02; H01B 1/12; C07D 333/38; H01G 9/00
USPC ....... 2/69; 549/4, 72; 252/500; 361/516, 517, 361/519, 530, 525–529; 438/584, 638; 29/25.01, 25.03
See application file for complete search history.

(56) References Cited

U.S. PATENT DOCUMENTS 4,978,780 A * 12/1990 Fikentscher et al. ............ 562/42
5,723,655 A * 3/1998 Uno et al. ........................ 562/58

(Continued)

*Primary Examiner* — Khanh Tuan Nguyen
*Assistant Examiner* — Danny N Kang
(74) *Attorney, Agent, or Firm* — US Naval Research Laboratory; Roy Roberts

(57) ABSTRACT

A redox-active conductive polymer includes a charged tether. An interpenetrating network including such a conducting polymer can be switched between two states of diffusivity (porosity) by application of a voltage. Such a material can be useful in breathable protective clothing, controlled release, intelligent sensing/filtration, novel separation processes, nanomanufacturing, and other areas.

18 Claims, 9 Drawing Sheets

(51) Int. Cl.
    *C08G 65/332* (2006.01)
    *C08G 65/334* (2006.01)
    *H01G 9/028* (2006.01)

(56) References Cited

U.S. PATENT DOCUMENTS

| | | | |
|---|---|---|---|
| 6,051,679 | A | 4/2000 | Leclerc et al. |
| 6,219,222 | B1 | 4/2001 | Shah et al. |
| 6,665,169 | B2 | 12/2003 | Tennent et al. |
| 6,706,218 | B2 | 3/2004 | Lucht et al. |
| 6,867,281 | B2 * | 3/2005 | Martin et al. ............ 528/373 |
| 6,905,586 | B2 | 6/2005 | Lee et al. |
| 7,001,669 | B2 | 2/2006 | Lu et al. |
| 7,025,324 | B1 | 4/2006 | Slocum et al. |
| 7,033,476 | B2 | 4/2006 | Lee et al. |
| 2003/0088032 | A1 | 5/2003 | Luebben et al. |
| 2007/0270508 | A1 * | 11/2007 | Liu ............................ 516/53 |
| 2008/0069971 | A1 | 3/2008 | Keersmaecker et al. |
| 2008/0166564 | A1 | 7/2008 | Rostovtsev et al. |
| 2008/0182844 | A1 | 7/2008 | Bjergarde et al. |
| 2010/0073847 | A1 | 3/2010 | Martin et al. |

\* cited by examiner

ELASTOMERIC COMPOSITES WITH TETHER-CONTAINING, CONDUCTING POLYMERS FOR NANOSCALE DIFFUSION CONTROL

CROSS-REFERENCE TO RELATED APPLICATIONS

This application claims benefit under 35 U.S.C. §120 as Continuation-In-Part of U.S. patent application Ser. No. 12/564,270 filed on Sep. 22, 2009, which in turn claims benefit under 35 U.S.C. §119(e) of U.S. Provisional Application No. 61/098,905, filed on Sep. 22, 2008.

BACKGROUND

A need exists for selective control of diffusion at a nanoscale level.

BRIEF SUMMARY

Selective control of diffusion is achieved through the use of conductive polymers, particularly tether-containing polythiophenes, embodiments of which are disclosed in commonly-assigned U.S. Patent Application Publication No. 2010/0073847, incorporated herein by reference.

In one embodiment, a material comprises an interpenetrating polymer network comprising a compound having the formula:

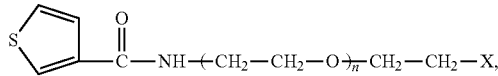

wherein X is a sulfonate salt, a phosphonate salt, a carboxylate salt, or a boronate salt and wherein n is an integer from 2 to 10; wherein the material repeatably switches between an open state and an closed state upon receiving a voltage.

In another embodiment, a material comprises an interpenetrating polymer network comprising:
a compound having the formula:

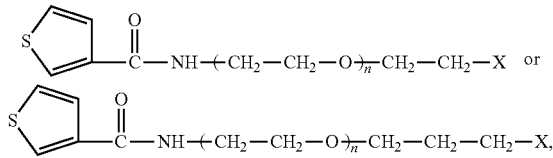

wherein X is a sulfonate salt, a phosphonate salt, a carboxylate salt, a cyclic moiety comprising a negatively-charged nitrogen, or a boronate salt and wherein n is an integer from 2 to 10; wherein the material repeatably switches between an open state and an closed state upon receiving a voltage.

In a further embodiment, the compound is selected from the group consisting of poly(3-{2-[2-(2-{2-[(thiophene-3-carbonyl)-amino]-ethoxy}-ethoxy)-ethoxy]-ethoxy}-propane-1-sulfonic acid) and poly(3-{2-[2-(2-{2-[(thiophene-3-carbonyl)-amino]-ethoxy}-ethoxy)-ethoxy]-ethoxy}-ethane-1-sulfonic acid).

In another embodiment, a method of modulating the diffusivity of a material comprises reducing the material to decrease its diffusivity and oxidizing the material to increase its diffusivity, wherein the material comprises a compound having the formula:

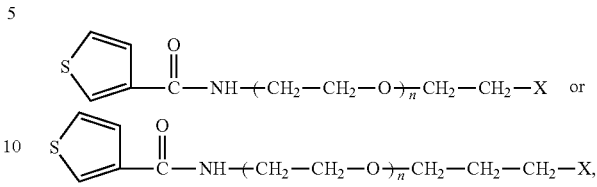

wherein X is a sulfonate salt, a phosphonate salt, a carboxylate salt, a cyclic moiety comprising a negatively-charged nitrogen, or a boronate salt and wherein n is an integer from 2 to 10. The reducing and oxidizing are preferable accomplished by the application of an electric voltage.

DETAILED DESCRIPTION

Definitions

Figure 1:
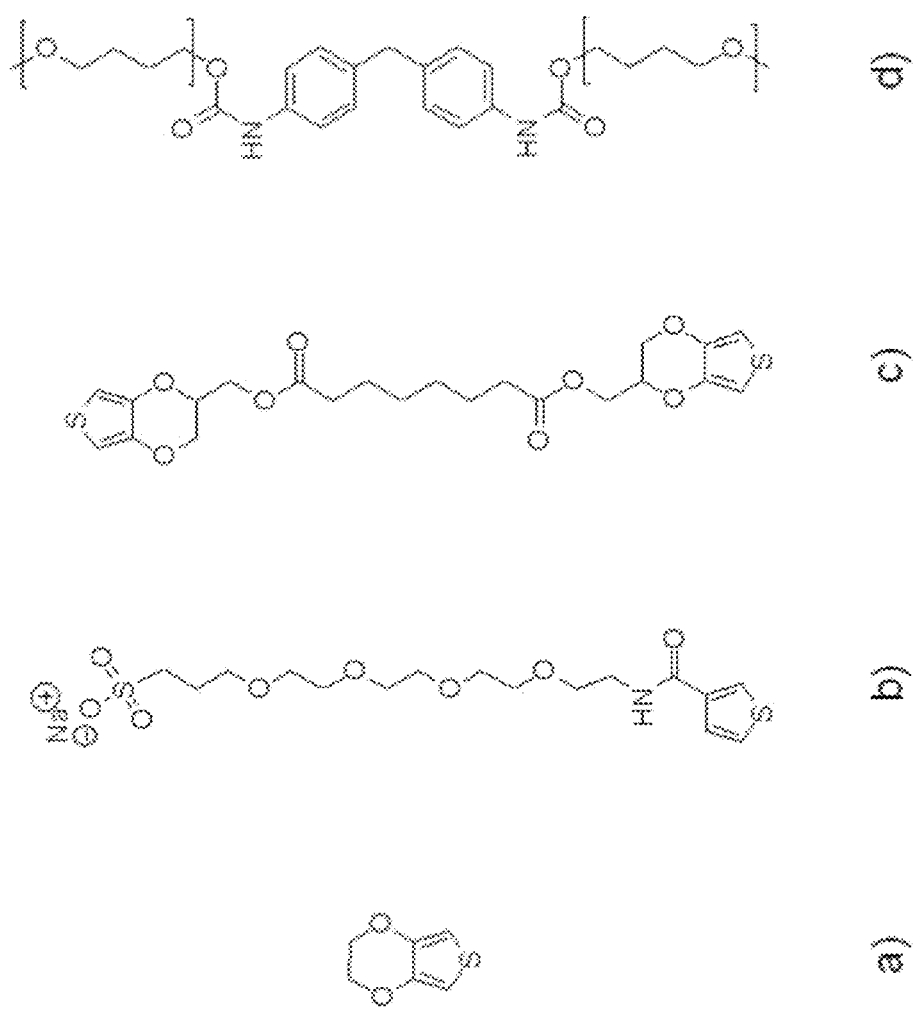
FIG. 1 shows termonomers and polyurethane for a conducting polymer network: a) 3,4 ethylenedioxythiophene (EDOT), b) TP-OEG-SO$_3$ monomer (poly(3-{2-[2-(2-{2-[(thiophene-3-carbonyl)-amino]-ethoxy}-ethoxy)-ethoxy]-ethoxy}-propane-1-sulfonic acid)), c) EDOT-ODA-EDOT crosslinker, and d) ESTANE MVT75 polyurethane.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, the terms "garment" and/or "clothing" include protective suits that fully cover the body, other types of protective garments, and more conventional clothing items.

As used herein, the term "interpenetrating polymer network" refers to a network comprising a conducting polymer intimately commingled with another material (such as a support matrix), and optionally including additional components.

Description

New materials having nano- or mesoscale porosities that can be reversibly changed on command are of great interest in many applications. They are expected to be useful in breathable protective clothing, controlled release, intelligent sensing/filtration, novel separation processes, nanomanufacturing, and other areas.

In the area of chemical protection, such new materials may have a major impact. Although standard chemical protective equipment (CPE) such as clothing have been improving for decades and can provide highly effective protection from chemical, biological, radiological, and/or nuclear threats (such as airborne chemical warfare (CW) agents), they have certain drawbacks. Prior art protective garments that provide breathability do not provide sufficient protection against a broad spectrum of threats. However, wearing more fully protective CPE can quickly diminish the performance of personnel because it is cumbersome and cannot readily dispel body heat. It also can cause difficulties in communication, sensory perception, and physical coordination. Therefore, CPE has been carried as an auxiliary to be donned only if threat is imminent or already present. This action usually requires from four to eight minutes and personnel are at risk of exposure to agent during this time. Also, it is necessary that personnel always keep CPE close at hand. If protective equipment could be made so that it can be worn at all times, and does not degrade performance, the above drawbacks could be eliminated. One can envision a clothing material that is comfortable to the wearer in the absence of CW agents, but is able to be "switched" to a protective, impermeable state if agent is present.

Described herein is an interpenetrating network (IPN) material with a conducting polymer having a charged tether. The IPN can be reversibly switched between two conducting states by the application of about plus one volt and minus one volt. The tethers may intramolecularly ion-pair to provide charge neutralization to the polymer when it is in its oxidized (doped) state, providing open pathways for water vapor transport, or breathability. When the polymer is switched to its reduced (dedoped) state, the freed tethers are allowed to "random walk" in the surrounding nanoregions, and thus obstruct movement of airborne species such as organic vapor. See FIG. 4. Thus the tethers serve as "nanogates" that are open when the polymer is oxidized, and closed when the polymer is reduced. The switching of the redox states is reversible, and actuated by the application of small voltages (such as about ±0.8 to 1.2 volts, with a total absolute voltage change of about 1.8 to 2.0 volts). This effect is reversible over a large number of cycles.

The switchable nature of the IPN allows for applications in CPE, particularly protective clothing, which should have improved permeability (breathability) for comfort while at the same time have the capacity to instantaneously and reversibly lower its permeability to agent molecules by application of the small voltage. When the membrane is in its "closed" (reduced) state, it blocks transport of agent. When the threat is removed, a second voltage application returns the membrane to its "open" (oxidized), breathable state. Both states are bistable.

The interpenetrating networks described herein comprise a conducting polymer intimately commingled with a support matrix. Preferably, an interpenetrating network also includes a crosslinker and a room-temperature ionic liquid (RTIL). Most preferably, the RTIL is absorbed into the IPN, leaving the IPN dry to the touch. In this case, the RTIL remains as a component of the IPN because it has essentially no vapor pressure and thus does not evaporate. This state of the IPN being dry to the touch is considered to be the absence of liquid electrolyte.

Exemplary components of conductive polymers include poly(3-{2-[2-(2-{2-[(thiophene-3-carbonyl)-amino]-ethoxy}-ethoxy)-ethoxy]-ethoxy}-propane-1-sulfonic acid), referred to as "poly(TP-OEG-SO$_3$)," and poly(3-{2-[2-(2-{2-[(thiophene-3-carbonyl)-amino]-ethoxy}-ethoxy)-ethoxy]-ethoxy}-ethane-1-sulfonic acid), which has been termed poly(TP-OEG-SO$_4$). More generally, it is expected that compounds having the formula:

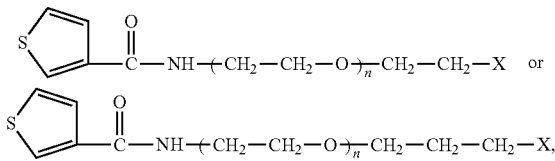

wherein X is a sulfonate salt, a phosphonate salt, a carboxylate salt, a cyclic moiety comprising a negatively-charged nitrogen, or a boronate salt and wherein n is an integer from 2 to 10, will be effective in forming conductive polymers useful in creating the described interpenetrating networks. IPN materials incorporating a conducting polymer having a charged tether (as in the compounds of this paragraph) are sometimes described herein as "Tether-IPN," whereas "Control-IPN" materials use a conducting polymer lacking a charged tether.

Poly(TP-OEG-SO$_4$) is described in commonly-owned U.S. Patent Application Publication No. 2010/0073847. As noted therein, this polymer can exhibit an active, reversible nanoscale gating effect. Cyclic voltammetry data allowed for calculating liquid-phase ion diffusivities in the polymer as a function of its oxidation state.

For a material to function in an intended use as a protective membrane, for protection against chemical warfare agents, for example, it is preferable that it can be "opened" and "closed" in its dry state with no liquid electrolyte present. For this to be achieved, some form of solid electrolyte must be present to allow charge compensation, or ion-pairing necessary for charge balancing whenever the membrane is cycled between its "open" (oxidized) and "closed" (reduced) states. It was found this that could be achieved with small amounts (3-7 wt %) of room-temperature ionic liquids (RTILs) added to the IPN. The RTIL absorbed into the IPN, leaving it dry to the touch and remaining as a permanent component since it lacks vapor pressure and thus will not evaporate. The RTILs used are insoluble in water, and so are unlikely to wash out upon exposure to aqueous solutions. It was further found that the addition of milled conducting carbon fibers (CFs) in small amounts (10-18 wt %), when present with the RTIL, allowed the IPNs to be fully and reversibly "switched" from the "open" to their "closed" states in the absence of liquid electrolyte.

The exemplary "IPN 1" composite comprises 10-18 wt % milled conducting CFs, 3 to 7 wt % RTILs, along with poly (TP-OEG-SO$_3$), a polymer chain crosslinker, and a support matrix. The term "IPN 2" refers to a control IPN similar to IPN 1, but with poly(3'4'-dimethyl-[2,2';5',2"]-terthiophene) in place of poly(TP-OEG-SO$_3$), so that is lacks the charged tether found in IPN 2.

FIG. 1 shows termonomers and polyurethane for an IPN 1 conducting polymer network: a) 3,4 ethylenedioxythiophene (EDOT), b) TP-OEG-SO$_3$ monomer, c) EDOT-ODA-EDOT crosslinker, and d) ESTANE MVT75 polyurethane used as a support matrix in this embodiment of IPN 1. Polymerization of EDOT, TP-OEG-SO$_3$ monomer (FIG. 2), and EDOT-ODA-EDOT polymer chain crosslinker in the presence of the solvated polyurethane and milled carbon fibers resulted in an adherent, homogeneous rubbery solid that blended well with the filter support. The crosslinker is based on two 3,4 ethylenedioxythiophene moieties connected by a bis-octanoic acid moiety. Its purpose was to contribute to the mechanical strength of the polymer and prevent liquid-phase dissolution of the poly(TP-OEG-SO$_3$) chains.

The support matrix in this embodiment is the ESTANE MVT 75 polyurethane. It is a thermoplastic polymer based on aromatic and ether repeat units, and is compatible with the poly(TP-OEG-SO$_3$) polymerization and redox chemistries. Its function was to further increase the mechanical strength and processability of the material while providing breathability. Its chemical composition and "free volume" (interconnected nanoporosity) allow it to have high moisture vapor transport capabilities. This makes it attractive for inclusion in materials development strategies for the creation of breathable protective clothing. Non-woven nylon (in particular, one having a pore size of 0.1 microns) was also successfully used as a support matrix, and found to be mechanically strong and not degraded by the polymerization solvent or the iron (III) oxidant. Other materials believed to be suitable to function as a support matrix include wool, polyester, cotton, and combinations of these with each other and/or with polyurethane and/or nylon.

The milled carbon fibers (CFs) assist in the electronic conductivity of the material, and may act to bridge conducting polymer-rich microregions that are separated by polyurethane-rich microregions. They are 50 microns in length, on average. As relatively small amount of carbon fibers (~15 wt % or less) were used, as higher levels could result in undesired electrical shorting. Quantities of about 10% by weight have also been used with success. They are included to improve charge percolation, and are also thought to increase the electric field strength and distribution in the IPN when the switching voltages are applied. Their presence in the polymerization solution causes its viscosity to increase slightly, which we have found improves its processability The room-temperature ionic liquid (RTIL) 1-methyl-3-ethyl imidazolium-bis-(perfluoroethylsulfonyl)imide (Emim-Tf$_2$) is added via ethanol carrier solvent after IPN synthesis. Its purpose is to provide free ions for charge-balancing, and assist in electron transport processes. RTILs have zero vapor pressure (they do not evaporate), and have moderate ionic conductivities (1 to 10 S/cm). A further advantage is that they are insoluble in water. This component was introduced into the membranes using a 30 wt % RTIL solution in ethanol, resulting in RTIL loadings of between 3% and 7 wt % relative to IPN mass, and the membrane remained macroscopically dry with no tack. The presence of the RTIL was not discernable visually. Gravimetric studies performed over 60 days showed that there was no evaporative loss of IL, as expected.

The RTIL component is preferably present at levels of ~6 wt %, which corresponds to about a 1:1 molar ratio with the OEG-sulfonate tether. Ionic liquids such as Emim-Tf$_2$ have very low vapor pressures, and thus have extremely low evaporation rates. For our application, it appeared to be an excellent choice for at least two reasons. First, the cationic imidazolium is known to form complexes with the ($\sigma^-$) oxygens of polyethylene glycol or OEG, which would help localize the RTIL molecules in the regions around the tethers and in close proximity to the CP main chains. Second, the Tf$_2$ anion can readily exist as a free ion. This allows the Emim cation to provide charge compensation for the freed sulfonate tethers when the IPN is in its closed state. The large size of the Tf$_2$ anion and the presence of the electron-withdrawing fluorination contribute to delocalization of the electron density, and consequently high polarizability. Electrical conductivity data gathered for ionic liquids with the Tf$_2$ anion show pronounced ion dissociation, with ionic conductivities similar to electrolyte solutions used in electrochemistry. These RTILs have recently been found to dissociate to an additional degree when diluted by addition of 10% v/v water, demonstrating ~14% dissociation at 25° C. Because of the hydrophilic nature of the sulfonated OEG tether chains, the IPN contains a small fraction of water, determined to be 5 to 7 wt % by thermogravimetric analysis. Simulations and spectroscopic studies have shown that Tf$_2$ interacts strongly with water solute, forming Tf$_2$ . . . HOH . . . Tf$_2$ hydrogen-bonding complexes that stabilize the lone anion. Therefore, the presence of small quantities of water within the IPN fabric would permit this interaction and facilitate anion stabilization. Finally, surface tension studies on Tf$_2$-containing ILs show that dispersion forces between all species are strong enough to allow the fluid to behave thermodynamically like an ionic solution, allowing the appearance of free ions. The ability of the Emim-Tf$_2$ RTIL to readily dissociate in this manner is believed to allow the IPN to be switchable as a macroscopically "dry" material, in the absence of bulk liquid electrolyte.

Figure 2:
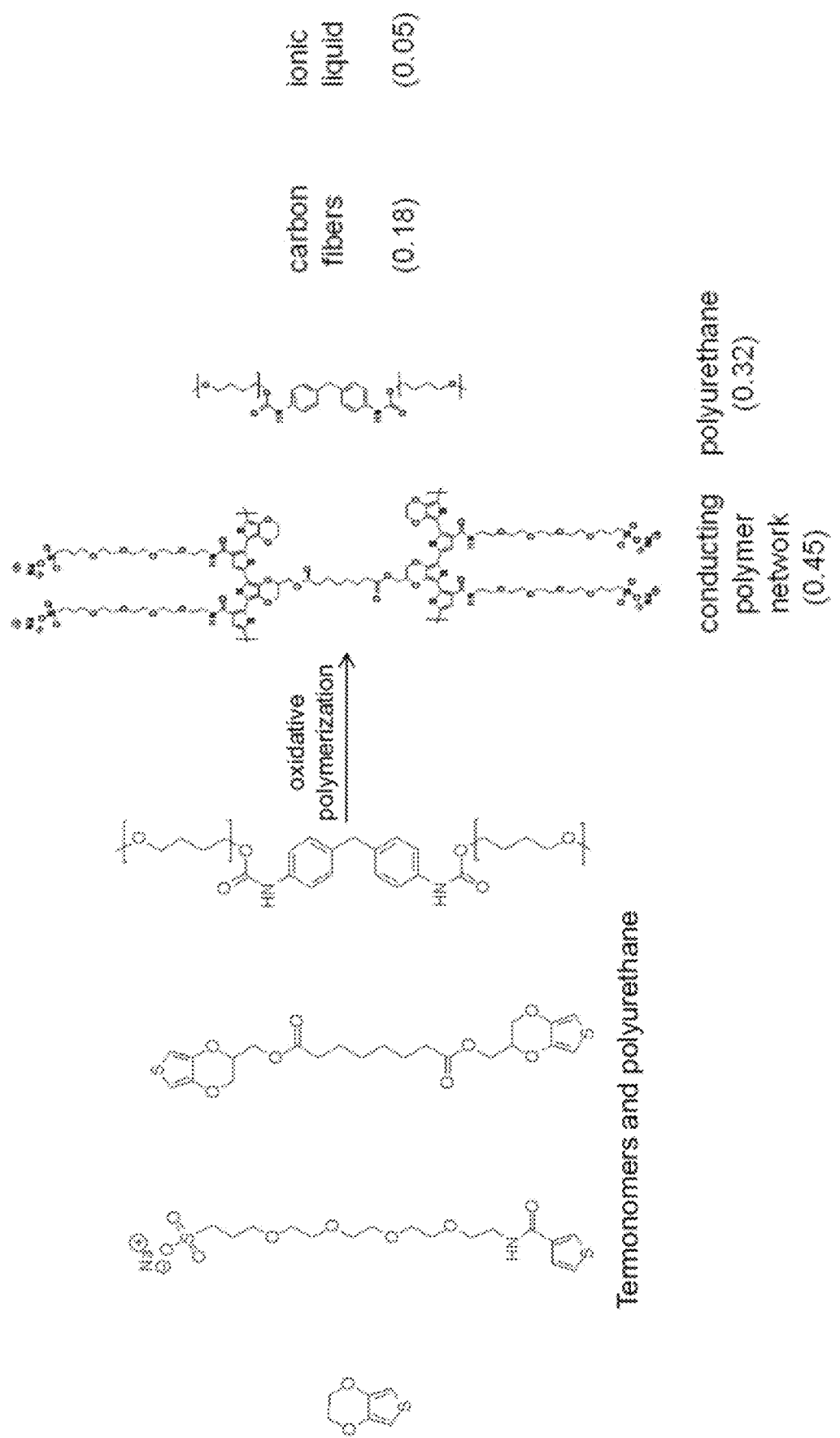
FIG. 2 shows an illustrative embodiment of the synthesis of an interpenetrating network (IPN) from several components with their corresponding weight fractions. Carbon fibers are added before polymerization and ionic liquid is added after polymerization. The room-temperature ionic liquid (RTIL) component was introduced by pipetting 11 μL of a 30 wt % solution of 1-methyl-3-ethyl imidazolium-bis-(perfluoroethylsulfonyl)imide (Emim-Tf$_2$) ionic liquid in ethanol to the filter section.

FIG. 2 shows an illustrative embodiment of the synthesis of an interpenetrating network (IPN) from several components with their corresponding weight fractions. The IPN was formed by statistical copolymerization of the starting materials. The polymerization was carried out using iron (III) tosylate in the stoichiometric amount of 2.5 moles Fe$^{+++}$ to 1.0 moles thiophene/EDOT repeat unit. The weight ratios between the TP-OEG-SO$_3$, EDOT-ODA-EDOT, EDOT, and polyurethane can be seen in FIG. 2. Ionic liquid is added after polymerization. The ionic liquid component was introduced by pipetting 11 μL of a 30 wt % solution of 1-methyl-3-ethyl imidazolium-bis-(perfluoroethylsulfonyl)imide ionic liquid in ethanol to the filter section.

It was found that the interpenetrating network (IPN) material can be switched in the "dry" state in the absence of liquid electrolyte, from an "open" state where it allows rapid passage of organic vapor, to a "closed" state where it greatly restricts the passage of organic vapor, by application of a −0.9 volt bias. It has been further shown that it can be "dry-switched" in the reverse direction, causing it to re-"open" from the "closed" state, by applying a +1.0 V bias. Here, in the presence of 50% relative humidity the "closed" state mostly blocked permeation of chloroethyl ethyl sulfide (a mustard gas stimulant, referred to as "CEES") vapor, whereas the "open" state permitted it. The voltage- (or redox-) induced changes in the permeability of the IPN also appeared as substantial changes in the impedance response of the material, as expected.

Figure 3:
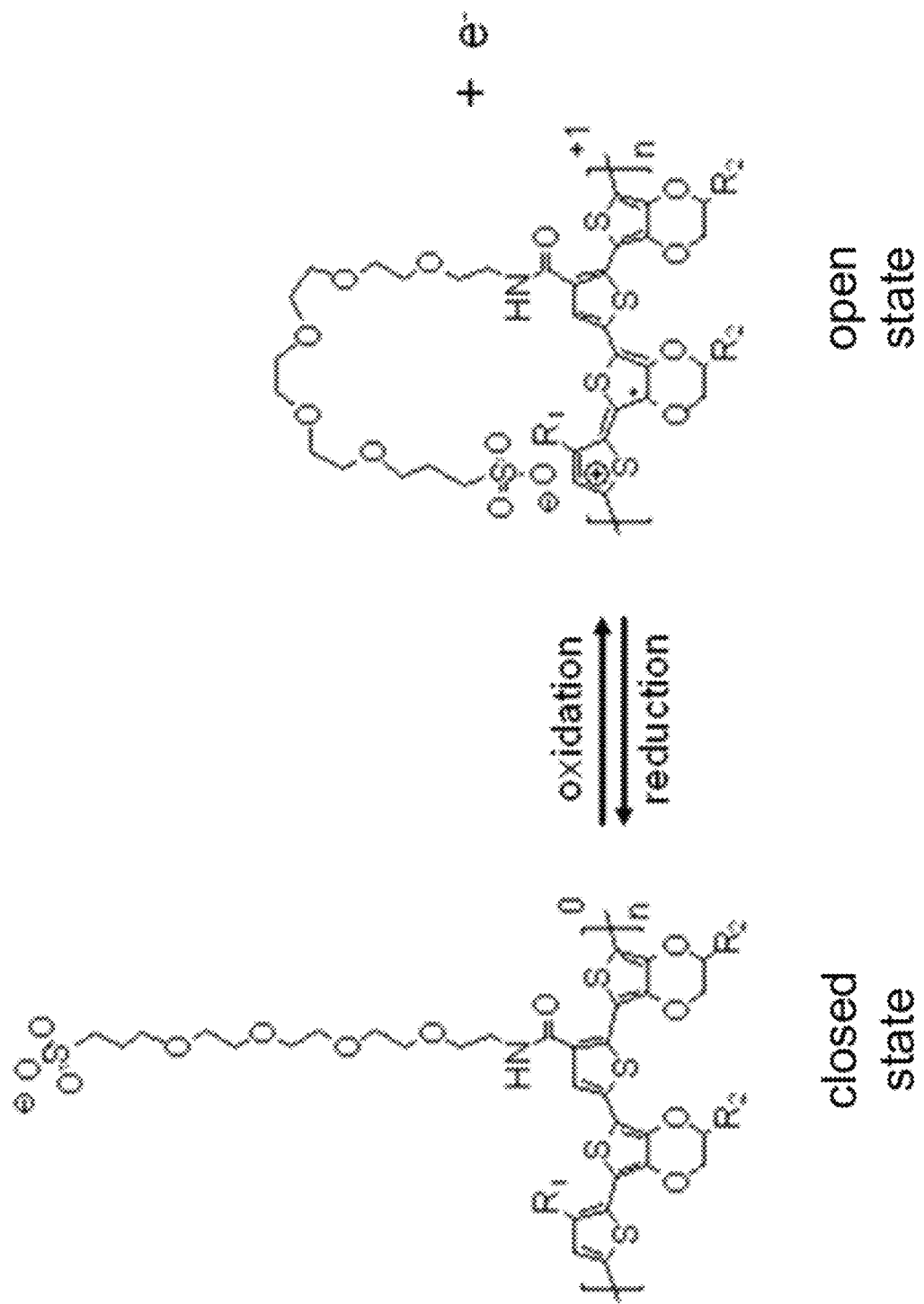
FIG. 3 shows a redox switching mechanism of a conducting polymer backbone, where "R$_1$" denotes tether side-chain, and "R$_2$" denotes alkyl chain crosslinker or hydrogen atom, omitted for clarity).
Figure 4:
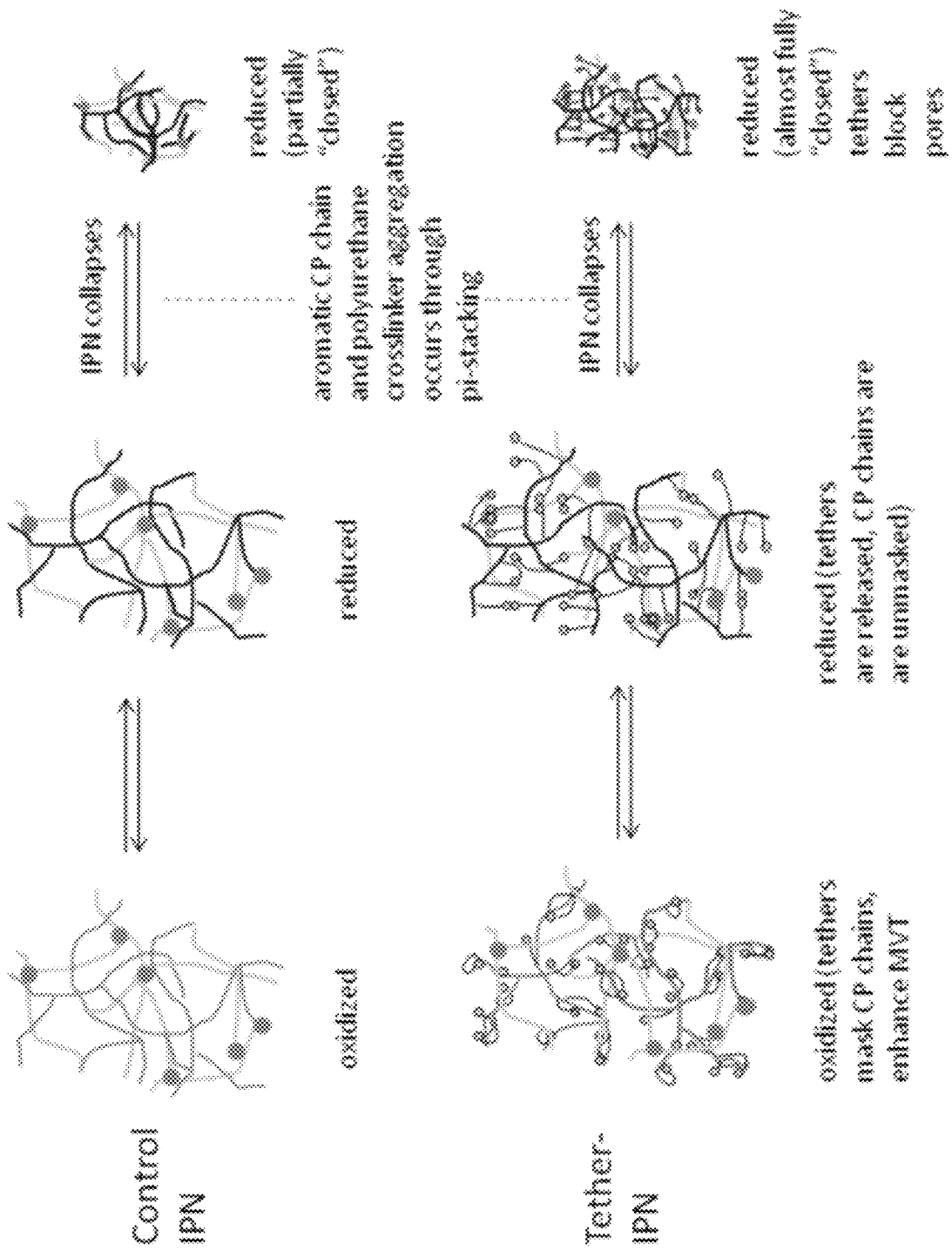
FIG. 4 is a schematic of a proposed open-close mechanism showing IPN collapse in both the control IPN and tether IPN during redox switching of the conducting polymers. Lines representing conductive polymer are shown in a darker state when reduced, while lines representing a co-polymer (for example, polyurethane) are shown unchanged. Small circles are shown at the end of the OEG-sulfonate tether. Larger circles represent aromatic crosslinking units.

A molecular explanation for the switching behavior is proposed in FIG. 3, which shows a redox switching mechanism of a conducting polymer backbone, where "$R_1$" denotes tether side-chain, and "$R_2$" denotes alkyl chain crosslinker or hydrogen atom, omitted for clarity. The reversible intramolecular ion-pairing configuration proposed in FIG. 3 is believed to account for the observed influence on ion diffusivities between the redox states of the material. The ion-pairing configuration shown there is an example of "self-doping", wherein a negatively-charged group that is attached to the conducting polymer main chain is able to participate in charge compensation. Because of steric hindrances and the fact that oxidized polythiophenes generally contain an upper limit of approximately one positive charge per two to four repeat units, it is necessary to assume that less than 100% of the tether population is able to adopt the configuration shown. The scheme proposed in FIG. 3 is a fairly simple but plausible molecular mechanism that accounts for the large changes in diffusivities. The observed changes could also arise from another scenario wherein the oxidized polymer serves to anchor the sulfonate termini in configurations that are both intra- and intermolecular. In both configurations, the OEG chains will be more rigid than in the case where the tether is free. One consequence of this chain stiffness may be the appearance of multiple pathways for solute diffusion. When the polymer is reduced, the released tethers will enter a relaxed state where they experience a higher configurational entropy that may enable them to act as effective blockers of solute diffusion. Also, charge repulsion between the sulfonate termini will help the relaxed tethers to distribute themselves uniformly into the nanoscale regions surrounding the poly (TP-OEG-SO$_3$) main chains As a control, IPN 2 was made, using the conducting polymer poly(3'4'-dimethyl-[2,2'; 5',2"]-terthiophene), which does not have a sulfonate tether, and included CFs and RTILs in the same concentration as in IPN 1. When in its as-synthesized, "oxidized" state, its impedance behavior was measured in the standard manner. When subjected to CEES vapor tests in its oxidized state, IPN 2 showed a permeability CEES vapor that was intermediate to the "open" and "closed" states of IPN 1. The voltage bias of −0.9 V was then applied to IPN 2 to reduce it, and the membrane was CEES vapor tested again. IPN 2 showed very little change in permeability (a decrease of ~8%, which is within the run-to-run variation of duplicate samples), as expected. Comparison of the plots of total impedance vs. frequency showed that virtually no change in impedance resulted from the voltage application to IPN 2, indicating that it is not able to be "switched" in the absence of electrolyte. This control experiment indicates that the tether moiety of IPN 1 plays a key role in the "switching", thus the "opening" and "closing" of the IPN 1 membrane FIG. 4 is a schematic of a proposed open-close mechanism showing IPN collapse in both the control IPN (IPN 2) and tether IPN (IPN 1) during redox switching of the conducting polymers. Lines representing conductive polymer are shown in a darker state when reduced, while lines representing a co-polymer (for example, polyurethane) are shown unchanged. Small circles are shown at the end of the OEG-sulfonate tether. Larger circles represent aromatic crosslinking units. It is known that when PEDOT is in its reduced state, the aromatic repeat units experience Van der Waals attraction, causing neighboring chains to pack together in dense aggregates. In the model of the Tether-IPN actuation, when the sulfonated tether side chains are oriented by the oxidized conducting polymer (CP) state in self-doping configurations, neighboring CP main chains are largely masked from one another. Thus they do not aggregate. The IPN is in its open state. Since the tethers are anchored at both ends, their configurational entropy is relatively low. This may impede their ability to block diffusion of small molecules. When the CP is switched into its reduced state, the CP main chain becomes electrically neutral, and the charged termini of the tethers are released. The CP main chains become exposed to one another, and they begin to pi-stack and aggregate. The freed tethers have a higher configurational entropy and block the interstitial spaces between the CP chains and the polyurethane chains. Their high entropy also may allow them to become more effective in impeding diffusion of small molecules. The CP now resembles a classical polymer "brush." Also, the termini may experience mutual repulsion because of their like negative charges. This would cause them to distribute themselves through the nanoscale spaces in a relatively homogeneous manner, improving the ability of the IPN to block transport of small molecules. This scenario is consistent with what is seen in the TEM images of FIG. 8. Finally, the aromatic regions of the CP main chain may aggregate with the aromatic bis-benzamides of the polyurethane chains, enhancing the collapse process of the entire IPN. This phenomenon is depicted in FIG. 4. The denser nature of the closed vs. open IPN has been quantified by nitrogen absorption studies and water absorption studies above.

Diffusivity values described herein may be measured by various methods, including cyclic voltammetry and by measuring water vapor transport. For example, cyclic voltammetry studies may be performed at 18° C. in a sealed cell using a CHI 660C Workstation, with a solvent system of 4:1 toluene:acetonitrile (by volume) containing concentrations of t-butylammonium hexafluorophosphate ranging from 300 mM to 0.1 mM.

Using electrochemical impedance spectroscopy (EIS) it has been shown that the dry IPN 1 can successfully undergo at least five "open-close" cycles, actuated by application of ±1.2 volts. The EIS studies indicate that ion diffusivities in the membrane vary by many thousand-fold as it is cycled through the "open" and "closed" states, with high diffusivities occurring in the "open" state and low ones in the "closed" state. The membrane was modeled using electrical circuit analogs, and have gained insight into material performance through analysis of the impedance data. The IPN in the "open" state allows water vapor transport (WVT) rates of as high as 1400 g/m$^2$ day, at 40° C. and 50% relative humidity. In contrast, under the same conditions a control IPN without tether (IPN 2) allowed a WVT rate of only 129 g/m$^2$ day. High WVT rates such as those displayed by the "open" IPN are important for the material to be breathable. Also, for the "open" and "closed" states of the IPN, pore area and volume measurements were undertaken using BET nitrogen adsorption techniques. The "closed" state was brought about by "switching"

in the dry state by applying a −0.9 or −1.0 V bias. The average pore surface areas were found to be ~3.5 to 4.5-fold higher in the "open" vs. "closed" states of the material. This is a direct indication that the former state has larger average pore sizes than the latter, and provides diffusion pathways that are relatively accessible and allow rapid transport of small compounds, including water vapor. It is likely that such pathways do not exist in the "closed" state of the material.

Figure 5:
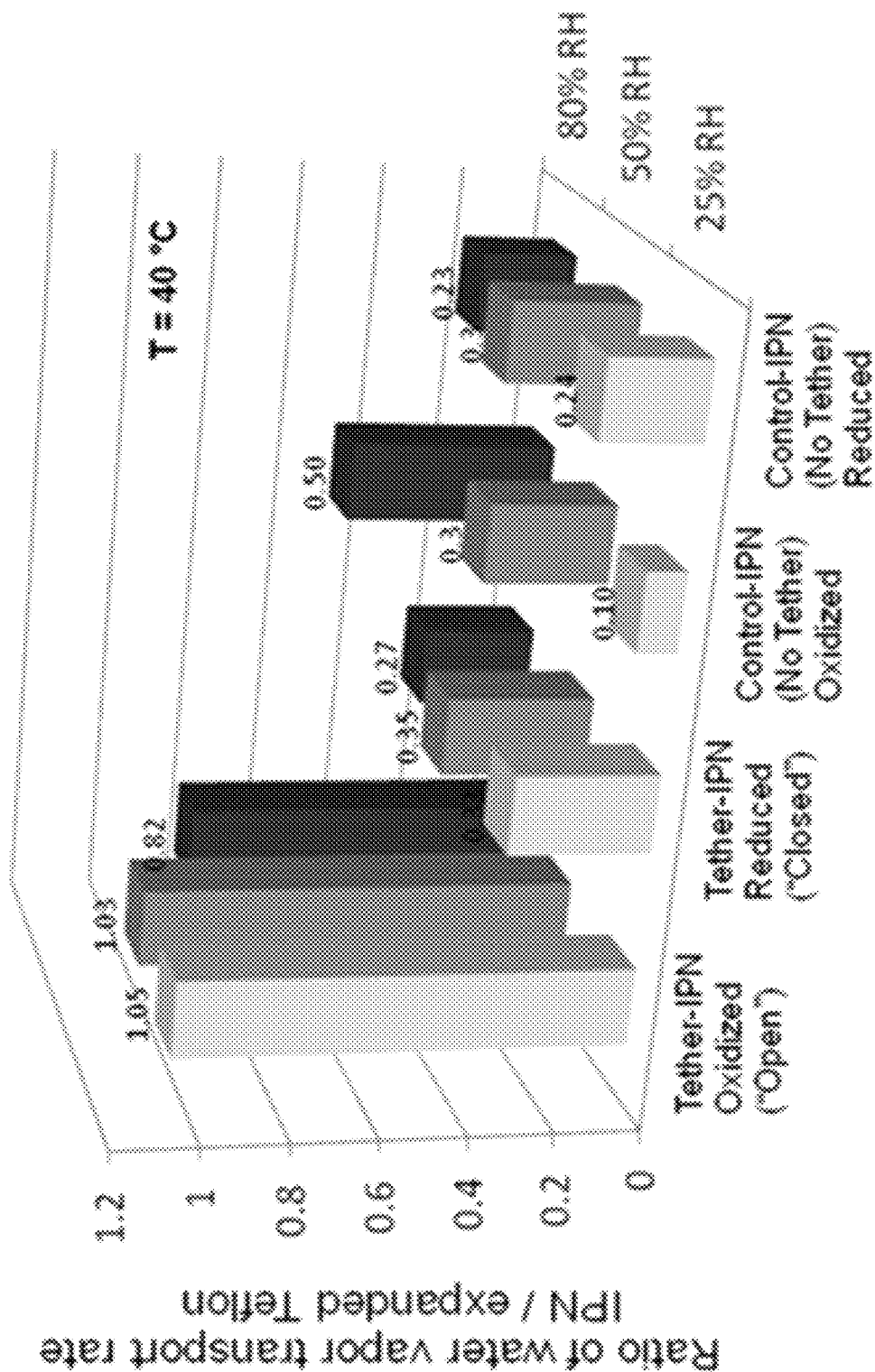
FIG. 5 is a comparison of moisture vapor transport rates. The IPNs in their oxidized and reduced states are compared, versus expanded Teflon.

FIG. 5 shows results of moisture vapor transport (MVT) measurements that were performed across Nylon-supported IPN 1 samples (shown as Tether-IPN oxidized and Tether-IPN reduced) and control IPN 2 samples (shown as Control-IPN oxidized and Ccontrol-IPN reduced). Samples were secured in a two-chambered diffusion cell. Using flow controllers, the relative humidity (RH) in the right-hand chamber was adjusted to 25%, 50%, and 80% at 40° C. while the RH in the left-hand second chamber was recorded. This allowed us to determine the amount of water vapor passing through the sample as a function of time. The ratio of MVT for each IPN sample vs. expanded Teflon (ePTFE) (MVT of IPN/MVT of ePTFE) is shown as a function of RH (25, 50 and 80%) in FIG. 6. ePTFE transports water vapor at very high rates compared to other clothing materials. The "open" IPN allows MVT at nearly the same rate as that of the ePTFE. For this set of experiments, the standard deviation ranged from ±9% to 13%. The "closed" IPN allows significantly (~70%) less MVT, indicating that it can hinder transport of molecules as small as water. This result is consistent with the TEM images that indicate large differences in pore sizes between the open and closed states. It is also interesting that for both the open and closed states, MVT rates are nearly independent of RH. This is in contrast to the MVT characteristics observed for other types of breathable fabrics. MVT through the control IPN in its oxidized state was significantly lower than the Tether IPN, and appeared to have some dependence on relative humidity. MVT through the control IPN in its reduced state was comparable to the Tether-IPN in its reduced state and did not demonstrate RH dependence. These results suggest that the presence of the tether facilitates the desirable characteristic of high MVT in the Tether-IPN open state. However, MVT is significantly diminished in its closed state. The high MVT of the oxidized state of the Tether-IPN compared to the Control IPN, and the comparable MVT in both reduced states suggests that the tether plays an important role in creating a pore structure that is conducive to high MVT through the Tether-IPN open state. The MVT through the closed state of the Tether-IPN is nearly identical to that through the reduced Control-IPN. Therefore, in the closed state of the Tether-IPN, the tether itself appears to play a minimal role in MVT.

An enclosed, temperature-controlled computerized test apparatus was constructed to allows performance of diffusivity/permeability studies on the membrane materials that involve the simultaneous presence of water vapor and vapor of a chemical weapon simulant. Using the apparatus with simulant vapor in conjunction with a power supply, the present inventors demonstrated that IPN 1 samples (supported by Nylon, dimensions 1.6 cm²×1.6 cm²) can be transformed from their "open" to their "closed" states by application of a −0.9 V bias in the absence of liquid electrolyte. In the "open" state, the IPN permitted the passage of benzene vapor, but after the IPN was "closed" the amount that could be passed through was lowered by 7 to 11 fold. This experiment was performed at 40° C. with no humidity present, and similar results were found when the experiment was repeated at 50° C. Thus, it was demonstrated that the IPN 1 can be "dry-switched" from an "open" to a "closed" state where it greatly restricts the passage of organic vapor. Furthermore, in separate experiments with chloroethyl ethyl sulfide (a mustard gas stimulant, referred to as "CEES") vapor, the present inventors showed that the IPN 1 can be transformed from a "closed" state to an "open" state by application of a +1.0 V bias. In the "closed" state, the IPN nearly completely blocked the passage of CEES vapor, but after the IPN was "opened" the amount that could be passed through was increased by ~150-fold. This experiment was performed at 40° C. and 50% relative humidity. Thus, it has been established that the IPN described herein can be "dry-switched", after exposure to humidity, from a "closed" to an "open" state where it allowed passage of simulant vapor.

Figure 6:
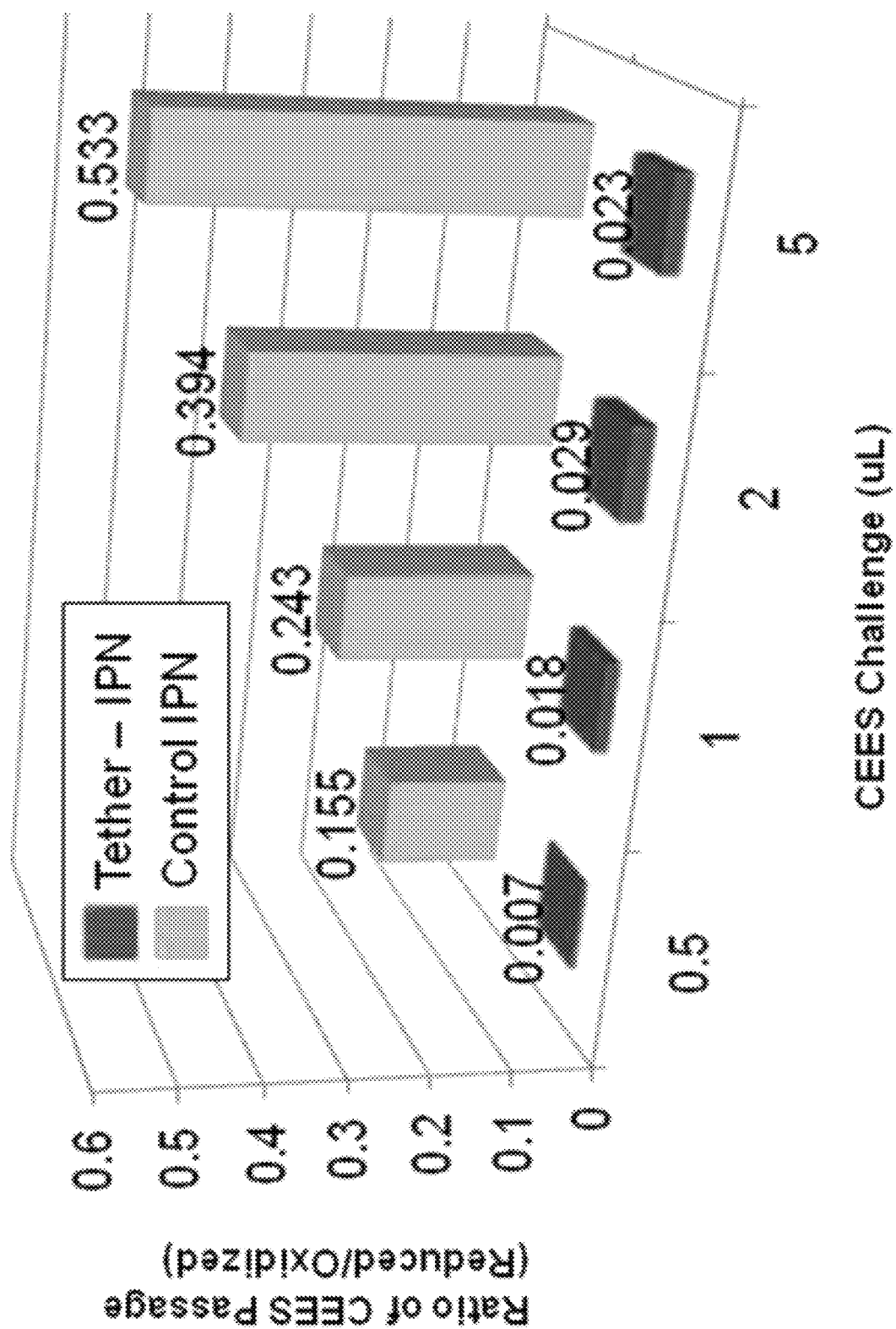
FIG. 6 shows ratios of passage of chemical weapon simulant CEES through the reduced vs. oxidized states of the IPNs.

FIG. 6 shows ratios of passage of chemical weapon simulant CEES through the reduced vs. oxidized states of the IPNs. The conditions were temperature of 40° C., relative humidity=50%. Error bars are ±14%. The ratios of CEES vapor fluxes through the reduced vs. oxidized states of the IPNs "open" vs. "closed" IPNs are shown. At the challenge level of 0.5 µL, the ratio is 0.7% for the Tether-IPN. Thus its closed state permits ~140-fold less CEES passage than its open state. As the challenge level is increased to 5 µL, this ratio remains near 2% to 3%. In contrast, the ratio for the Control IPN steadily increases to ~0.5. This suggests that fundamentally different mechanisms govern CEES diffusion in the Tether-IPN vs. the Control-IPN.

Figure 7:
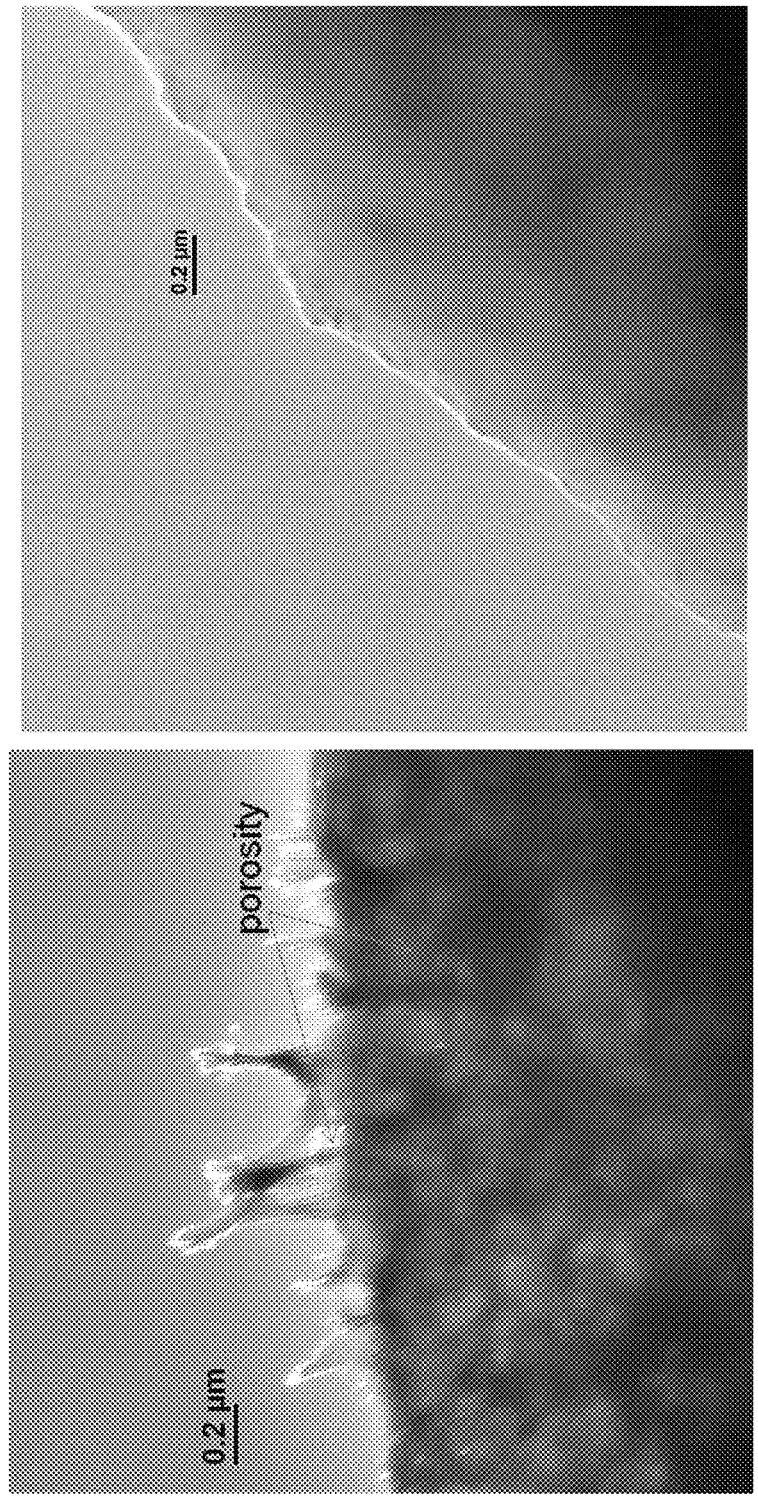
FIG. 7 shows transmission electron microscopy (TEM) images of IPN in its a) open and b) closed states.

FIG. 7 shows transmission electron microscopy (TEM) images of IPN in its a) open and b) closed states. Transmission electron microscopy (TEM) was used as a direct means of visualizing the open and closed states of the IPN material. Suitable material samples were prepared by casting the IPN onto copper TEM grids or copper wire, and introducing the proportionate amount of the Emim-Tf$_2$ room temperature ionic liquid (RTIL). Samples were switched to their closed state by carefully attaching the working, counter, and reference electrodes in the manner described above and subjecting them to a reducing voltage of −1.0 volts. EIS was routinely employed to verify whether the closed state had been attained. The TEM image of the oxidized as-synthesized open state is shown in FIG. 3a, and that of the reduced closed state is shown in FIG. 3b. The open state clearly has what appears to be regions of high and low porosity—large areas of light and dark regions, which represent electron-deficient and electron-rich regions, respectively.

Together, they form an image resembling a sponge-like porous structure. The open state pore-size distribution may be in the meso- and nanoscale range. The closed state, FIG. 7 b), is morphologically very distinct from the open state, FIG. 7 a). It does not show the sponge-like characteristics of the open state, but instead resembles a dense homogeneous phase with no evidence of porosity. The images for the open and closed states are consistent with the model introduced with regard to FIG. 4.

The described IPN is able to exert powerful control over ion transport in the absence of liquid electrolyte. These ratios are even higher than those found in the presence of liquid electrolyte, which ranged from 1200 to 3200. It may be possible to increase ion mobilities in the material by using lithium as a counter-cation for the sulfonate terminus, instead of sodium (the former has a molecular weight of 7; the latter, 23). Also, the presence of the oligoethylene glycol tethers should facilitate the transport of the lithium ions even more so than sodium ions.

The reversible nanoscale gating effects exhibited by the IPN described herein provide unique properties. Its ability to fully function in the "dry" state in the absence of liquid electrolyte is a very important asset, allowing it to be incorporated into protective fabrics and garments. Its ability to be cycled between the oxidized, open state and the reduced, closed state at low voltages (between −1.0 and 1.0 volts) rather than higher voltages is an asset as well.

Methodology

Chemical Syntheses

Synthesis of TP-OEG-SO$_3$ Precursor (compound 2).

Figure 8:
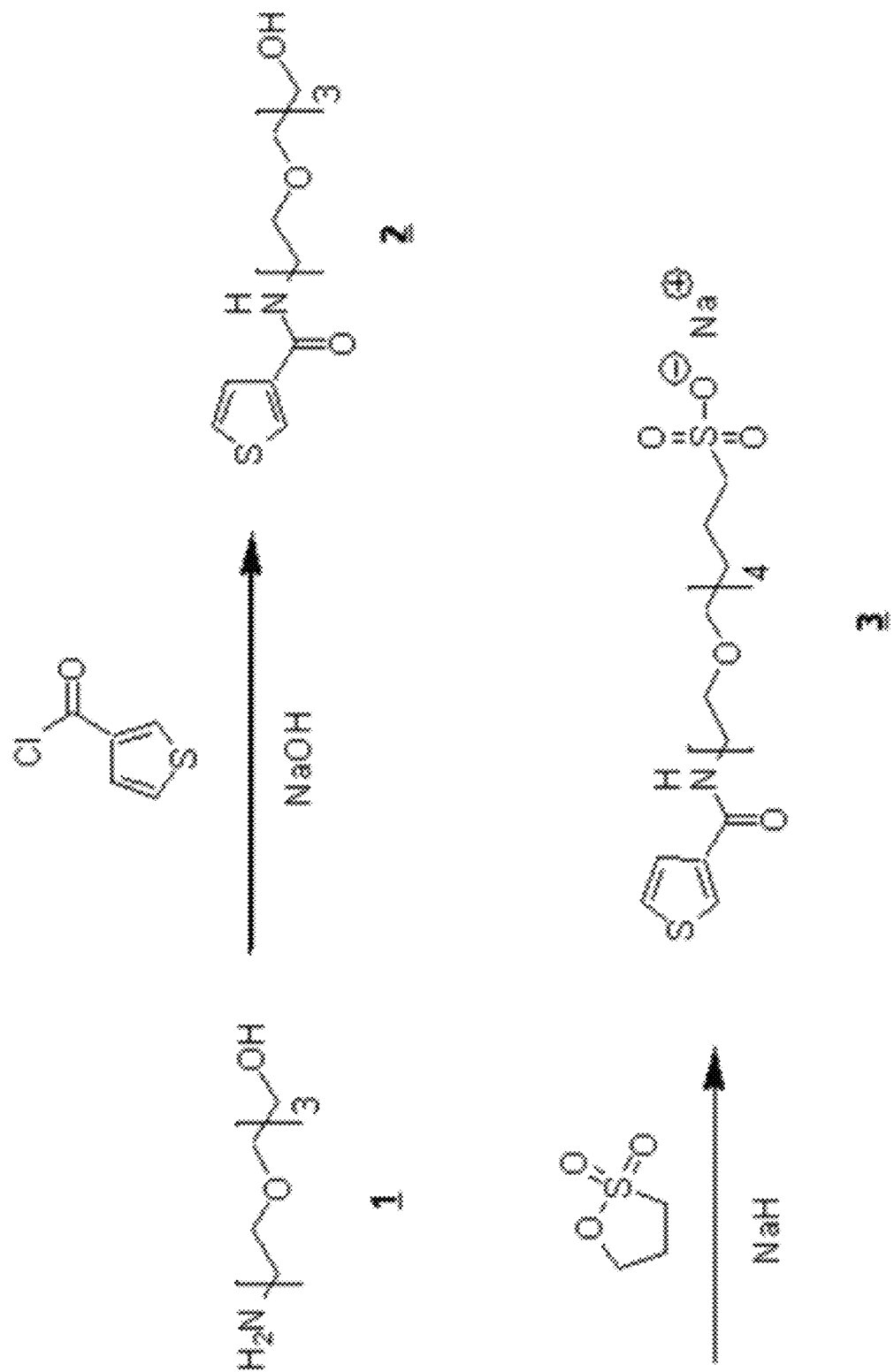
FIG. 8 shows the synthesis of TP-OEG-SO$_3$.

A mixture of thiophene carboxylic acid (2.5 g, 19.5 mmol), a 1.5 molar excess of oxalyl chloride and 1 drop of DMF in 10 mL of benzene was stirred overnight at room temperature. The solvent was removed under vacuum. The acid chloride obtained was dissolved in THF (5 mL) and added dropwise at 0° C. to a stirred mixture of 1 (3.05 g, 16.0 mmol) in 50 mL of water and 1.28 g of NaOH. The reaction was stirred overnight at room temperature. The solution was acidified to pH=4 with 1 N HCl aqueous solution. The product was extracted using ethyl acetate to give a yellow liquid. Gradient column chromatography in silica gel with ethyl acetate eluent and then methanol yielded 3 g (62%) of the final product 2 as viscous yellowish liquid (FIG. 8). $^1$H NMR (400 MHz, CDCl$_3$, δ in ppm): 3.6-3.8 (m, —CH$_2$—O—, 16H), 6.75 (br, —NH, —OH, 2H), 7.30 (d, —CH=CH—, 1H), 7.50 (d, —CH=C—S—, 1H), 8.0 (d, —CH=CH—, 1H).

Synthesis of TP-OEG-SO3 (compound 3).

Figure 9:
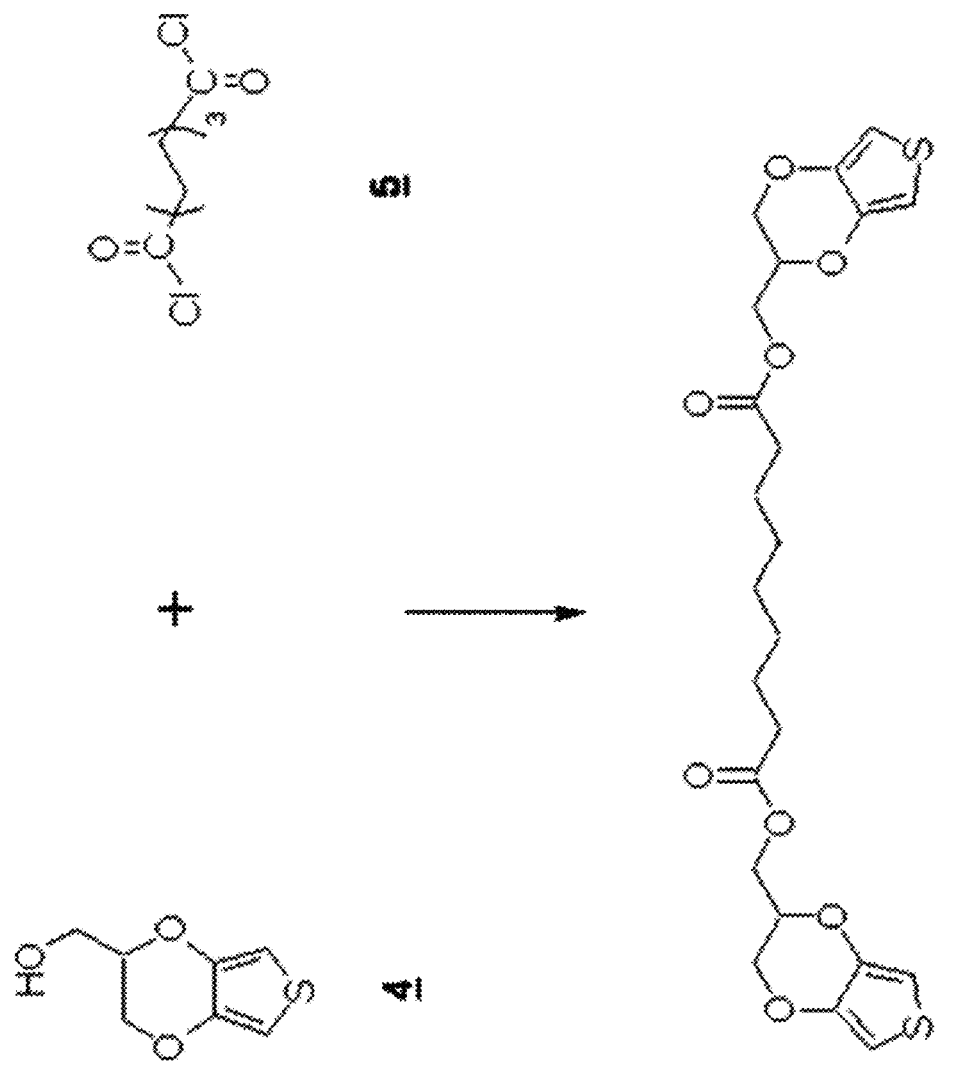
FIG. 9 shows the synthesis of the crosslinker EDOT-ODA-EDOT.

A mixture of 2 (4 g, 13.2 mmol) and NaH (0.33 g, 14 mmol) in 20 ml of dry THF under nitrogen, was stirred in a two-necked round-bottomed flask equipped with a condenser and dropping funnel. The mixture was heated to 60° C., and a solution of THF (10 mL) containing 1,3-propane sulfone (1.72 g, 14 mmol) was added dropwise. The mixture was heated for an extra two hours. After evaporation of the solvent, the product was purified by column chromatography in silica with CH$_2$Cl$_2$:MeOH (95:5) as the eluent mixture to yield a waxy white solid: yield 4 g (67%) (FIG. 9). $^1$H NMR (400 MHz, D$_2$O, δ in ppm): 1.95 (m, —CH$_2$—, 2H), 2.87 (m, —CH$_2$—, 2H), 3.5-3.8 (m, —CH$_2$—O—, 18H), 6.8 (br, —NH—, 1H), 7.30 (d, —CH=CH—, 1H), 7.50 (d, —CH=C—S—, 1H), 7.95 (d, —CH=CH—, 1H). Anal. calcd for C$_{16}$H$_{26}$NNaO$_8$S$_2$: C, 42.94; H, 5.86. Found: C, 42.20; H, 6.02.

Synthesis of octanedioic acid bis-(2,3-dihydro-thieno[3,4-b][1,4]dioxin-2-ylmethyl) ester (EDOT-ODA-EDOT) (compound 6).

A solution of 4 (EDOT-CH$_2$OH) (2.5 g, 14.53 mmol), dry pyridine (1.5 mL) and 10 mL of dry THF was added dropwise to a solution of octanedoic acid dichloride 5 (1.5 g, 7.11 mmol) in 15 mL of THF and stirred at 0° in an ice/water bath. The mixture was then stirred 24 hrs at room temperature. Water and dichloromethane were added and the organic phase was washed with a dilute solution of ammonium chloride, a saturated solution of sodium chloride and then dried over Na$_2$SO$_4$. The solvent was evaporated and the residue was subjected to column chromatography on silica gel with CH$_2$Cl$_2$ as the eluting solvent. The final product 6 was collected as an oil which crystallizes with time (FIG. 9). Yield: 3.2 g, 45%. $^1$H NMR (CDCl$_3$, TMS) δ (ppm): 1.20 (m, 4H, —CH$_2$—CH$_2$—), 1.56 (m, —CH$_2$—CH$_2$—, 4H), 2.30 (m, —CH$_2$—, 4H), 4.1 (m, —CH—O—, 4H), 4.5 (m, —CH—O—, 2H), 4.60 (m, —CH$_2$—O—, 4H), 6.1 (d, —CH—S—, 4H).

Synthesis of 3'4'-dimethyl-[2,2';5',2"]-terthiophene.

The synthesis of the trimeric thiophene 3'4'-dimethyl-[2,2'; 5',2"]-terthiophene (DMTP) was performed as reported in J. Marchand-Brynaert, M. Bouchet, et al, Tetrahedron, 52, (1996) 5591 and P. Blondin, J. Bouchard, S. Beaupre, et al Macromolecules, (2000) 33, 5874.

IPN Synthesis in Filter Supports.

The filter-supported IPN 1 was synthesized by blending a polyurethane-containing solvent with a second solvent containing TP-OEG-SO$_3$, EDOT-ODA-EDOT, and iron (III) tosylate oxidant, heating the mixture, and casting it into the support filter. Adherent IPNs were formed in filters composed of Nylon (0.1 micron pore size). The Nylon filters were originally circular in shape (4.7 cm diameter), and prior to use were cut into quadrants of equal area (4.3 cm$^2$ each), weighing ~24 mg. In a typical synthesis, 240 µL of THF containing 10 wt % polyurethane was added to 160 µL anisole containing 6 mg EDOT-ODA-EDOT, and 15 mg carbon fibers (GRA-NOC, 50 micron avg. length, Nippon Graphite Fiber Corp.) forming solution "1". The mixing was performed in a 1-cm diameter 5 ml vial. Next, 140 µL ethanol containing 24 mg TP-OEG-SO$_3$ was added to 200 µL ethanol containing 120 mg iron (III) tosylate hexahydrate oxidant, forming solution "2", again in a 1-cm diameter 5 ml vial. Solutions 1 and 2 were then mixed vigorously (2 was added to 1), and heated for 60 seconds in an oven, temperature 70° C. To permit full solubility of the polyurethane component, an additional 160 µL THF was added with mixing and the solution was allowed to heat with occasional mixing to accomplish complete dissolution of the polyurethane component (usually requiring ~60 seconds). Finally, four 170 µL aliquots of the solution were then separately deposited onto 4 cut filter supports (the sections were resting on a glass microscope slide, both the sections and the slide were pre-heated in the oven at 70° C.). The deposition was done by pipette, and the solution was deposited in a manner allowing complete and uniform coverage of the filter, without solution runoff. The polymerization was allowed to proceed overnight at 68° C. The IPN formed in the filter support and was dark blue in color because of the oxidized poly(TP-OEG-SO$_3$)/EDOT-ODA-EDOT. The samples were carefully removed from the glass slide and immersed in hot water for 30 seconds (stirring, 80-85° C.) to extract the iron (II) reaction byproduct as well as any unreacted iron (III). Thermogravimetric analysis was performed using a TA Instruments Model 2950 Thermogravimetric Analyzer with a temperature ramp of 10° C./min in the range 25° C. to 600° C. The results showed that the extraction procedure removed ~98% of the iron salts from the samples. The samples were then air-dried and stored at room temperature. Each filter section was found to contain ~12 mg of the IPN. Finally, the ionic liquid component was introduced by pipetting 11 µL of a 30 wt % solution of 1-methyl-3-ethyl imidazolium-bis-(perfluoroethylsulfonyl) imide ionic liquid in ethanol to the filter section. A corresponding procedure was used for the synthesis of IPN 2, with 15 mg DMTP used instead of 24 mg TP-OEG-SO$_3$. The amounts of the other reactants remained the same as in the synthesis of IPN 1.

General

Each and every document cited in this disclosure is incorporated herein by reference in its entirety.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as means-plus-function language unless the term "means" is expressly used in association therewith.

What is claimed is:

1. A material comprising:
an interpenetrating polymer network comprising:
a compound having the formula:

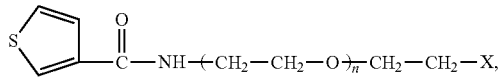

wherein X is a sulfonate salt, a phosphonate salt, a carboxylate salt, or a boronate salt and wherein n is an integer from 2 to 10;
wherein the material repeatably switches between an open state and an closed state upon receiving a voltage.

2. The material of claim 1, wherein said material exhibits an ion diffusivity in said open state of at least 350 times greater than in said closed state as measured by cyclic voltammetry.

3. The material of claim 1, further comprising a support matrix of polyurethane.

4. A material comprising:
an interpenetrating polymer network comprising:
a compound having the formula:

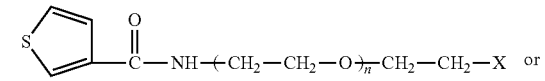

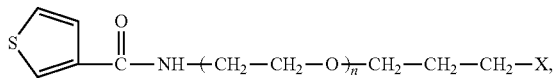

wherein X is a sulfonate salt, a phosphonate salt, a carboxylate salt, a cyclic moiety comprising a negatively-charged nitrogen, or a boronate salt and wherein n is an integer from 2 to 10;
wherein the material repeatably switches between an open state and an closed state upon receiving a voltage.

5. The material of claim 4, further comprising a support matrix and a room temperature ionic liquid.

6. The material of claim 5, wherein said support matrix is selected from the group consisting of polyurethane, nylon, wool, polyester, cotton, and combinations thereof.

7. The material of claim 4, wherein said ion diffusivity in said open state is at least 200 times greater than in said closed state.

8. The material of claim 4, wherein said switching is operable in the absence of a liquid electrolyte.

9. The material of claim 4, wherein in said open state, the material is effective to allow water vapor transport of as 1400 g/m² day or greater under conditions of 40° C. and 50% relative humidity.

10. The material of claim 4, wherein said compound is selected from the group consisting of poly(3-{2-[2-(2-{2-[(thiophene-3-carbonyl)-amino]-ethoxy}-ethoxy)-ethoxy]-ethoxy}-propane-1-sulfonic acid) and poly(3-{2-[2-(2-{2-[(thiophene-3-carbonyl)-amino]-ethoxy}-ethoxy)-ethoxy]-ethoxy}-ethane-1-sulfonic acid).

11. The garment of claim 10, further comprising a source of electrical power and a switch.

12. A garment incorporating the material of claim 4.

13. A filter for gas and/or liquid incorporating the material of claim 4.

14. A method of modulating the diffusivity of a material, the method comprising:
reducing the material to decrease its diffusivity and oxidizing the material to increase its diffusivity,
wherein the material comprises a compound having the formula:

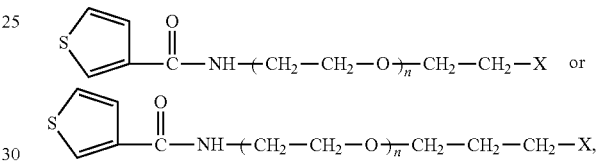

wherein X is a sulfonate salt, a phosphonate salt, a carboxylate salt, a cyclic moiety comprising a negatively-charged nitrogen, or a boronate salt and wherein n is an integer from 2 to 10.

15. The method of claim 14, wherein said reducing and oxidizing are accomplished by the application of an electric voltage.

16. The method of claim 14, wherein said compound is selected from the group consisting of poly(3-{2-[2-(2-{2-[(thiophene-3-carbonyl)-amino]-ethoxy}-ethoxy)-ethoxy]-ethoxy}-propane-1-sulfonic acid) and poly(3-{2-[2-(2-{2-[(thiophene-3-carbonyl)-amino]-ethoxy}-ethoxy)-ethoxy]-ethoxy}-ethane-1-sulfonic acid).

17. The method of claim 14, wherein said material further comprises a support matrix and a room temperature ionic liquid.

18. The method of claim 17, wherein said support matrix is selected from the group consisting of polyurethane, nylon, wool, polyester, cotton, and combinations thereof.

* * * * *